(12) United States Patent
Hatanaka et al.

(10) Patent No.: US 9,907,895 B2
(45) Date of Patent: Mar. 6, 2018

(54) CONTROLLER FOR LIFE SUPPORT DEVICE AND CONTROL METHOD THEREOF

(71) Applicant: TERUMO KABUSHIKI KAISHA, Tokyo (JP)

(72) Inventors: Youko Hatanaka, Kanagawa (JP); Takeharu Iwata, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 364 days.

(21) Appl. No.: 14/427,034

(22) PCT Filed: Sep. 26, 2012

(86) PCT No.: PCT/JP2012/006130
§ 371 (c)(1),
(2) Date: Mar. 10, 2015

(87) PCT Pub. No.: WO2014/049643
PCT Pub. Date: Apr. 3, 2014

(65) Prior Publication Data
US 2015/0238674 A1 Aug. 27, 2015

(51) Int. Cl.
*A61M 1/16* (2006.01)
*A61M 1/36* (2006.01)
*G06F 19/00* (2018.01)

(52) U.S. Cl.
CPC ........ *A61M 1/1601* (2014.02); *A61M 1/1698* (2013.01); *A61M 1/3666* (2013.01); *A61M 1/3667* (2014.02); *G06F 19/3406* (2013.01); *A61M 2205/17* (2013.01); *A61M 2205/702* (2013.01); *F04C 2270/0421* (2013.01)

(58) Field of Classification Search
CPC .............. A61M 1/3621; A61M 1/3667; A61M 1/3666; A61M 1/1006; A61M 1/3643
See application file for complete search history.

(56) References Cited

U.S. PATENT DOCUMENTS 6,123,726 A * 9/2000 Mori ...................... A61M 1/101
 600/17
6,808,508 B1 * 10/2004 Zafirelis ................ A61M 1/101
 604/131

(Continued)

FOREIGN PATENT DOCUMENTS

JP 2007014504 1/2007
WO 2004096322 A1 11/2004

*Primary Examiner* — Leslie Deak
(74) *Attorney, Agent, or Firm* — MacMillan, Sobanski & Todd, LLC

(57) ABSTRACT

A controller for a life support device, the controller having a control section in charge of sequence control, the controller includes: a first interface section transmitting an output state of the control section to each part in the life support device, and transmitting an output state of each part in the life support device to the control section; and a second interface section setting an output state in response to detection of a predetermined data sequence output from the control section, and maintaining the set output state until the second interface section receives the predetermined data sequence anew. A part of the life support device is driven via the second interface section.

5 Claims, 4 Drawing Sheets

(56) References Cited

U.S. PATENT DOCUMENTS

| | | | |
|---|---|---|---|
| 6,868,309 B1* | 3/2005 | Begelman | G06F 19/3481 422/107 |
| 2008/0214979 A1* | 9/2008 | Brugger | A61M 1/3626 604/6.1 |
| 2011/0106466 A1 | 5/2011 | Furmanski et al. | |
| 2011/0112595 A1 | 5/2011 | Solem et al. | |

* cited by examiner

CONTROLLER FOR LIFE SUPPORT DEVICE AND CONTROL METHOD THEREOF

TECHNICAL FIELD

The present invention relates to a controller for a life support device and a control method thereof.

BACKGROUND ART

Conventionally, a cardiopulmonary support device used for cardiopulmonary support is known as a typical extracorporeal circulation device, which is an example of a life support device. Such a device has an extracorporeal blood circulation circuit including an oxygenator, a centrifugal artificial heart (centrifugal pump), a controller, an oxygen supply source (oxygen cylinder), and the like (see Patent Document 1).

The cardiopulmonary support device functions in place of the heart and lungs of a patient being operated on or a patient in a state of cardiopulmonary arrest. A high degree of safety is required of the cardiopulmonary support device so that the cardiopulmonary support device does not stop while operating.

PRIOR ART DOCUMENT

Patent Document

Patent Document 1: Japanese Patent Laid-Open No. 2007-14504

SUMMARY OF INVENTION

Technical Problems

One method for ensuring the safety of the life support device is to form a duplex structure of a main controller and a sub-controller for controlling units constituting the life support device. This is because the sub-controller continues control even when the main controller stops due to some cause. Thus duplexing the controller can construct a safer system, but on the other hand complicates a circuit scale and invites an increase in size of the device and an increase in power consumption.

To deal with the problems of the complication of the circuit scale, the increase in size of the device, and the increase in power consumption, a constitution is considered in which a logic IC monitoring a stop or runaway of a microcomputer constituting a controller is provided to generate an alarm upon detecting a stop or runaway of the microcomputer. In this case, when a stop or runaway of the microcomputer is detected, the outputs of the microcomputer (controller) generally become indeterminate or are simultaneously turned off. Thus, for example a driving section for the centrifugal pump in the heart-lung machine device stops, so that a blood flow is stopped. Such stoppage of the blood flow is directly linked with life or death of the patient. It is thus desirable that a period of stoppage of the centrifugal pump in the heart-lung machine device be as short as possible.

The present invention has been made in view of the above problems. It is an object of the present invention to provide a life support device having a high degree of safety without increasing a circuit scale.

Technical Solution

A controller for a life support device according to a position mode of the present invention for solving the above problems has the following constitution.

A controller for a life support device, the controller having a control section in charge of sequence control, the controller including:

first interface means for transmitting an output state of the control section to each part in the life support device, and transmitting an output state of each part in the life support device to the control section; and second interface means for setting an output state in response to detection of a predetermined data sequence output from the control section, and maintaining the set output state until the second interface means receives the predetermined data sequence anew;

a part of the life support device being driven via the second interface means.

Advantageous Effect

According to the present invention, it is possible to provide a life support device having a high degree of safety while suppressing an increase in a circuit scale.

Other features and advantages of the present invention will become apparent from description in the following with reference to the accompanying drawings. Incidentally, in the accompanying drawings, the same or similar constitutions are identified by the same reference numerals.

DETAILED DESCRIPTION OF PREFERRED EMBODIMENTS

An embodiment of the present invention will hereinafter be described in detail with reference to the accompanying drawings.

Figure 1:
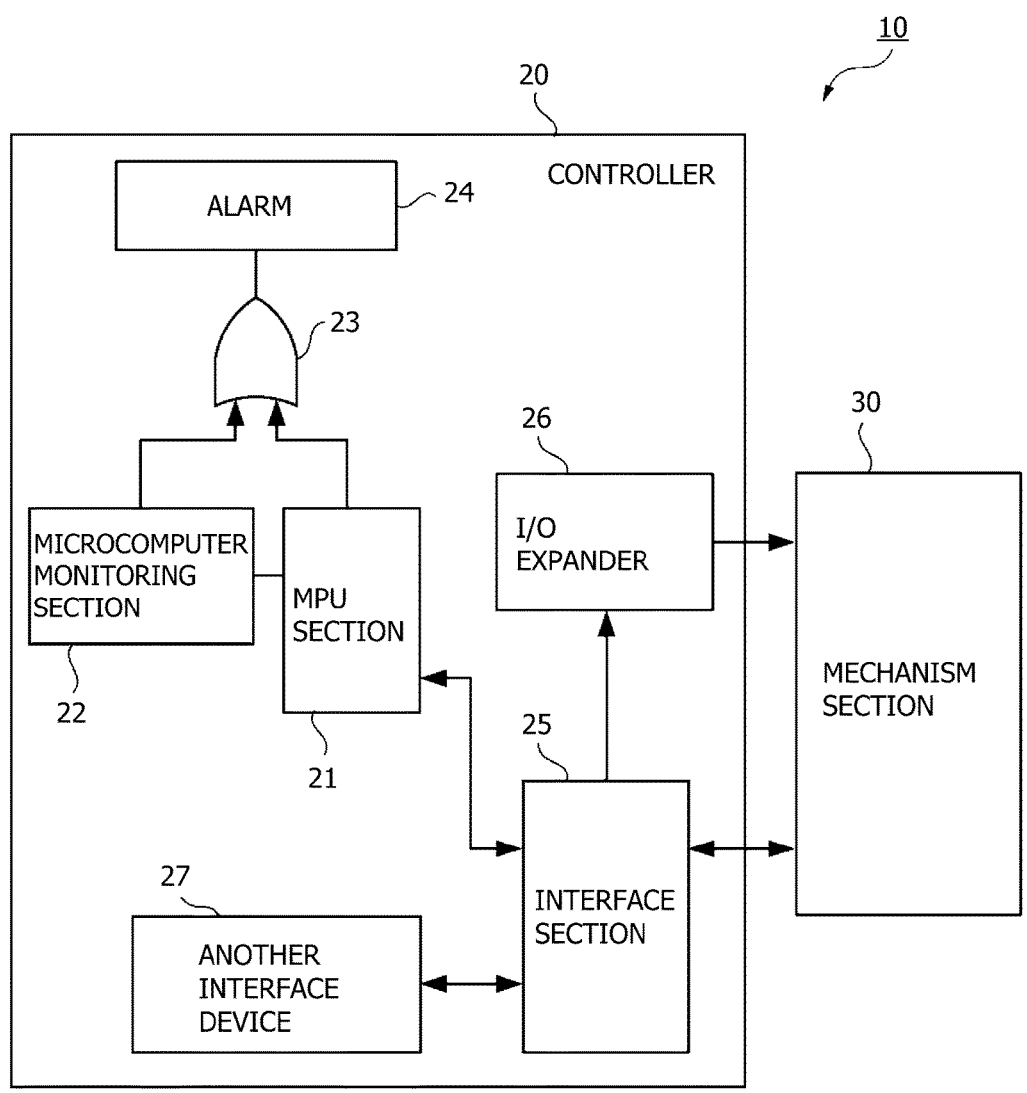
FIG. 1 is a diagram showing an example of general constitution of a life support device according to an embodiment of the present invention.

FIG. 1 is a block diagram of assistance in explaining an outline of a life support device 10 according to an embodiment. The life support device 10 includes a controller 20 and a mechanism section 30 of the life support device controlled by the controller 20. An MPU section 21 in the controller 20 performs various kinds of processing using a ROM as a program memory not shown in the figures, a RAM as a work memory, and the like. The MPU section 21 constitutes a microcomputer together with an interface section 25 and the like. The microcomputer thus implements various kinds of control including the driving of the mechanism section 30 in the life support device 10 by executing a program stored in the ROM. Incidentally, in the above description, a microcomputer is illustrated as a control section in charge of sequence control for the mechanism section 30. However, the control section is not limited to this. For example, an FPGA or the like may be used in place of the microcomputer.

A microcomputer monitoring section 22 monitors the occurrence of a failure such as a stop or runaway in the MPU section 21. When the microcomputer monitoring section 22 detects a stop or runaway, the microcomputer monitoring section 22 outputs an alarm output to an OR circuit 23. The OR circuit 23 drives an alarm 24 in response to an alarm output from at least one of the MPU section 21 and the microcomputer monitoring section 22. The alarm 24 is formed by an alarm lamp and/or buzzer, for example.

An input and an output of the MPU section 21 are connected to the interface section 25 as a first interface. An input and an output of the mechanism section 30 in the life support device 10 are connected to the MPU section 21. In addition, user interfaces such as a display section, an operating section, and the like are also connected as another input-output device 27 to the interface section 25 as the first interface section.

Further, a part of control output from the MPU section 21 is output to the mechanism section 30 indirectly via a second interface section. The second interface section is configured to set an output state for controlling one of more devices (i.e., actuators) in response to a predetermined data sequence output from the MPU section 21 and transferred to the second interface section via the first interface section, and to maintain the set output state until the second interface section receives another valid predetermined data sequence generated by MPU section 21 and transferred via the first interface section. An I/O expander 26 is used as the second interface section in the present embodiment. In the present embodiment, the I/O expander 26 and the MPU section 21 are connected to each other via the interface section 25. An I2C (Inter-Integrated Circuit) communication, for example, can be used as communication protocol between the MPU section 21 and the I/O expander 26, such that first interface section 25 is used by MPU section 21 to send the predetermined data sequences to I/O expander 26.

The output of the I/O expander 26 as the second interface section is used to drive a mechanism (i.e, an actuator) essential for life support operation by the life support device 10. Such a mechanism essential for the life support operation includes for example a centrifugal pump, a fast clip, and the like in an extracorporeal circulation device (heart-lung machine).

Generally, when the MPU section 21 stops or runs away unexpectedly, the microcomputer monitoring section 22 resets all of I/O states for safety, and gives an alarm by the alarm 24. Hence, when runaway or the like occurred in the MPU section 21, the mechanism essential for the life support operation would also be stopped if the mechanism was connected to the first interface since resetting of MPU section 21 would also reset interface section 25. Such a state of the mechanism essential for the life support operation being stopped before the life support device recovers needs to be shortened as much as possible. According to the controller 20 in the present embodiment shown in FIG. 1, the I/O expander 26 is not reset by the resetting of MPU 21. Instead, I/O expander 26 continues the present operating state of the mechanism(s) in mechanism section 30 to which it is connected. In order to change those operating states, the MPU section 21 needs to output the predetermined data sequence to change the output state of the I/O expander 26 as the second interface section. In the case where the MPU section 21 stops or runs away, there is almost no possibility of such a predetermined data sequence being output, and therefore the I/O expander 26 maintains a state immediately before the runaway or the stop of the MPU section 21. That is, the constitution which is driving-controlled via the I/O expander 26 can maintain a state of operation and does not stop immediately even when the MPU section 21 runs away or stops.

Hence, according to the present embodiment, the driving of the mechanism essential for the life support operation is maintained with a simple constitution even when the MPU section 21 stops or runs away. It is thus possible to shorten the state of the mechanism essential for the life support operation being stopped between the occurrence of trouble (start of notification by the alarm 24) to the solution of the trouble (resetting of the MPU section 21, for example) by a user. Description in the following will be made of an example of application to an extracorporeal circulation device as the life support device.

<General Constitution of Extracorporeal Circulation Device>

Figure 2:
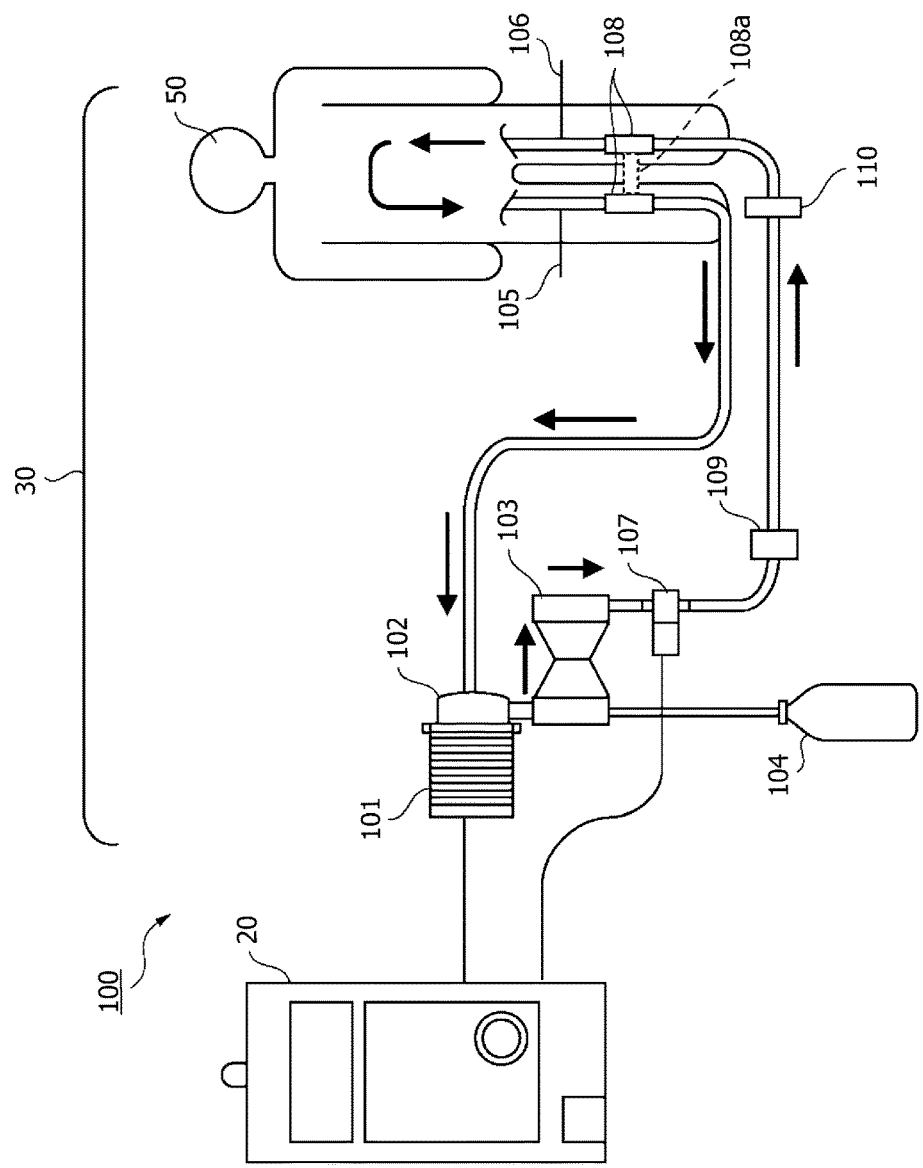
FIG. 2 is a block diagram showing an example of configuration of an extracorporeal circulation device as an example of the life support device.

FIG. 2 is a diagram showing an example of a general constitution of an extracorporeal circulation device 100 as the life support device 10 according to a first embodiment of the present invention. The extracorporeal circulation device 100 performs cardiopulmonary support operation (extracorporeal circulation and auxiliary circulation) used to perform a procedure referred to as PCPS (percutaneous cardiopulmonary support), for example. The mechanism section 30 of the extracorporeal circulation device 100 has an extracorporeal blood circulation circuit (hereinafter referred to as a circulation circuit) indicated by arrows in the figure. The extracorporeal circulation device 100 performs a priming operation, and thereafter extracorporeally circulates the blood of the subject 50 using the circulation circuit. Here, the priming operation refers to an operation of circulating a priming solution (for example a physiological saline solution) within the circulation circuit and removing air bubbles within the circuit in a state of the circulation circuit being sufficiently filled with the priming solution.

The extracorporeal circulation device 100 is provided with the controller 20 shown in FIG. 1, a motor 101, a centrifugal pump 102 driven by the motor 101, an oxygenator 103, an oxygen supply source 104, a catheter (vein side) 105, a catheter (artery side) 106, an air bubble sensor 107, a branch line 108, and a blood filter 109. Incidentally, connections between these constitutions are established by flexible tubes or the like, and the lumens of the tubes form a flow passage for the blood. The catheter (artery side) 106 sends the blood into the body of the subject 50. The catheter (vein side) 105 removes the blood from the body of the subject 50.

The centrifugal pump 102 is referred to also as a centrifugal artificial heart. The centrifugal pump 102 applies a pressure to the blood by driving an internally provided rotor, and thus circulates the blood within the circulation circuit. The motor 101 provides a rotational driving force to the rotor of the centrifugal pump 102. The oxygenator 103 performs blood circulation and blood gas exchange (addition of oxygen and removal of carbon dioxide, or the like). The oxygen supply source 104 is implemented by an oxygen cylinder, for example. The oxygen supply source 104 supplies oxygen to be added to the blood. The oxygen supplied from the oxygen supply source 104 is used for the gas exchange by the oxygenator 103.

The air bubble sensor 107 detects air bubbles flowing within the circulation circuit during priming operation or during blood circulating operation by a predetermined detecting method (ultrasonic wave, light, or the like). The blood filter 109 filters the blood, and removes air bubbles within the blood. A fast clamp 110 is used to stop the flow of the blood when the air bubble sensor 107 detects air bubbles during the blood circulating operation. The controller 20 controls the opening and closing of the fast clamp 110 according to an air bubble detection signal from the air bubble sensor 107.

The branch line 108 changes the flow passage of the circulation circuit. Specifically, when the blood of the subject 50 is circulated extracorporeally, the circulation circuit passing through the body of the subject 50 is constructed, and the blood is circulated outside the body of the subject 50, as shown in FIG. 2. In addition, during the priming operation, a branch line 108a is made to conduct, and the subject 50 side of the branch line 108 is closed. The path of the circulation circuit into the body of the subject 50 is thereby blocked to construct a circulation circuit passing only outside the body of the subject 50 (in other words, a circulation circuit not passing through the body of the subject 50). In the state of the branch line 108a conducting, the circulation circuit is internally filled with a priming solution, and the priming solution is circulated (without passing through the body of the subject). One or a plurality of air bubble discharge ports (not shown) for discharging air bubbles are provided on the circulation circuit. Air bubbles within the circulation circuit are discharged from the air bubble discharge port(s) by making the priming solution circulate so as to make a plurality of rounds within the circulation circuit.

The controller 20 performs centralized control of operation in the extracorporeal circulation device 100. The controller 20 for example supplies a control signal to a driving circuit that controls the motor 101 to drive the centrifugal pump 102, and obtains an air bubble detection result (sensor value) from the air bubble sensor 107 and controls the opening and closing of the fast clamp 110. The controller 20 also controls the above-described priming operation, for example.

In the following, brief description will be made of a flow of processing when the blood of the subject 50 is circulated extracorporeally by using the extracorporeal circulation device 100 shown in FIG. 2. Prior to a start of the extracorporeal circulation, the controller 20 controls the execution of the above-described priming operation. During the priming operation, a circulation circuit not passing through the body of the subject 50 is constructed using the branch line 108a. In addition, at this time, a priming solution supply source not shown in the figures is connected to the branch line 108a to supply the priming solution into the circulation circuit. The circulation circuit is thereby internally filled with the priming solution.

Then, when a driving signal is supplied to the motor 101 under control of the controller 20, and the centrifugal pump 102 is thereby driven so as to achieve a predetermined flow rate, the priming solution is circulated so as to make a plurality of rounds within the circulation circuit. Air bubbles within the circulation circuit are discharged from the air bubble discharge port(s) or the like as this circulation is made. At this time, the air bubble sensor 107 detects the air bubbles within the circulation circuit, and the controller 20 monitors the state of the air bubbles included within the circulation circuit on the basis of a result of the detection by the air bubble sensor 107.

Upon detecting that air bubbles have disappeared within the circulation circuit according to a predetermined criterion (details of the predetermined criterion will be described later), the controller 20 ends the priming operation. At the time of this ending, the controller 20 notifies the user that the priming operation is ended by using a display (not shown) and a speaker (not shown), or the like. Notified of the ending of the priming operation, the user closes the branch line 108a, and constructs a circulation circuit passing through the body of the subject 50 using the branch line 108. The controller 20 sets the flow rate of the blood, and drives the motor 101 so as to drive the centrifugal pump 102 at the set blood flow rate, thus extracorporeally circulating the blood of the subject 50.

When the extracorporeal circulation is started, the blood removed from the catheter (vein side) 105 passes through the centrifugal pump 102, and then enters the oxygenator 103. The oxygenator 103 performs gas exchange, that is, processes such as the addition of oxygen and the removal of carbon dioxide or the like, as described above. Thereafter, a filtered blood passed through the blood filter 109 and the like is sent from the catheter (artery side) 106 into the body of the subject 50. The processes from the removal of the blood to the sending of the blood are repeated, and thus the blood of the subject 50 is circulated extracorporeally. At this time, the controller 20 monitors whether the air bubble sensor 107 has detected air bubbles. When air bubbles are detected, the controller 20 sets the fast clamp 110 in a closed state to stop the flow of the blood.

The above description has been made of an example of the general constitution of the extracorporeal circulation device 100 according to the present embodiment and the flow of processes for the extracorporeal circulation. Incidentally, the constitution of the extracorporeal circulation device 100 shown in FIG. 2 is a mere example, and the constitution may be changed as appropriate. For example, a reservoir (storing blood) may be provided. In addition, in the above description, the motor 101 and the fast clamp 110 are directly related to the stopping of the flow of blood. In the present embodiment, the motor 101 and the fast clamp 110 are driven via the second interface section to thereby maintain the flow of blood at a time of runaway or a stop of the MPU section 21.

<Functional Configuration of Controller 20>

Figure 3:
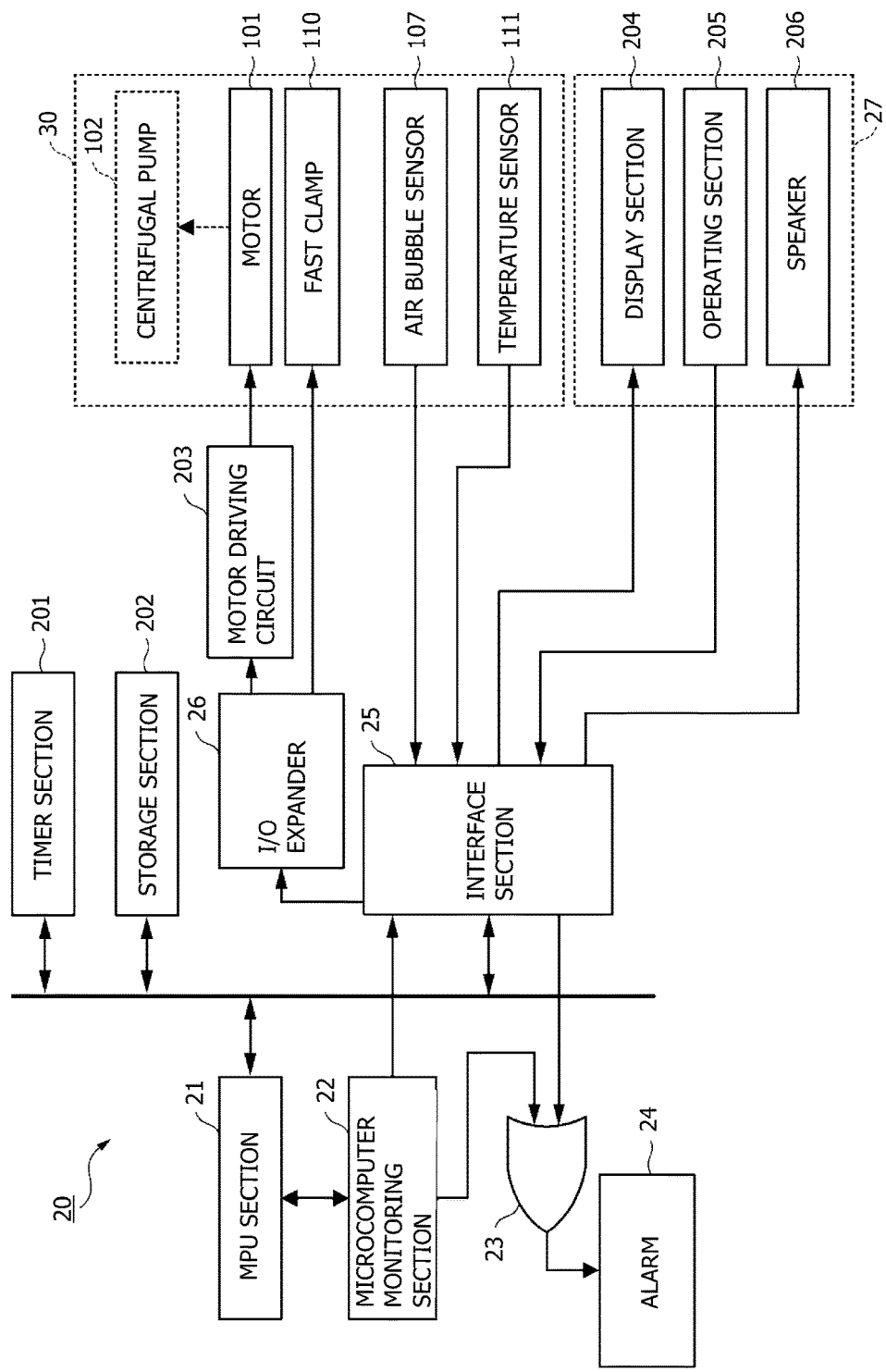
FIG. 3 is a block diagram showing an example of configuration of a controller for controlling the extracorporeal circulation device.

Next, referring to FIG. 3, description will be made of an example of functional configuration of the controller 20 applied to the extracorporeal circulation device 100 shown in FIG. 2. Incidentally, in FIG. 3, constitutions similar to the constitutions shown in FIG. 1 and FIG. 2 are identified by the same reference numerals.

In the controller 20, a timer section 201 provides a clock function to the controller 20. A storage section 202 is an external storage device of the MPU section 21. A program stored in the storage section 202 may be expanded in the RAM not shown in the figures within the MPU section 21 to perform processing. A motor driving circuit 203 drives the motor 101 according to an output of the I/O expander 26 as the second interface section. The motor driving circuit 203 drives the motor 101 according to an input rotational speed (digital value). Incidentally, the motor driving circuit 203 may be disposed within the housing of controller 20, or may be disposed in a separate housing for the mechanism section 30. Another output of the I/O expander 26 is used to drive the fast clamp 110. Thus, fast clamp 110 and motor driving circuit 203/motor 101 are examples of controlled actuators essential for life support operation. I/O expander 26 is directly connected to fast clamp 110 and motor driving circuit 203, but is indirectly connected to MPU section 21 via first interface section 25.

In addition, the interface section 25 as the first interface section is connected with the air bubble sensor 107 in the mechanism section 30 of the extracorporeal circulation device 100 and a temperature sensor 111 for monitoring the temperature of circulating blood. Incidentally, when the temperature sensor 111 indicates that the temperature of the blood has deviated from a predetermined range, an alarm is output. In addition, FIG. 3 shows a display section 204, an operating section 205, and a speaker 206 as another input-output device 27 connected to the interface section 25. The display section 204 is for example implemented by a display such as a monitor or the like (including an output section outputting an alarm as sound). The display section 204 displays various kinds of information for the user. The operating section 205 is for example implemented by various kinds of buttons or the like. Instructions from a medical worker are input to the operating section 205. Incidentally, a part or the whole of the display section 204 and the operating section 205 may be implemented as a touch panel having a sound speaker, for example. The speaker 206 provides the user with various kinds of notifications indicating an end of priming operation and the like.

Incidentally, when the microcomputer monitoring section 22 detects a stop or runaway of the MPU section 21, the microcomputer monitoring section 22 supplies the interface section 25 with a reset signal for safety to change all of output states of the interface section 25 to an off state. However, I/O expander 26 is unaffected by the reset signal.

Figure 4:
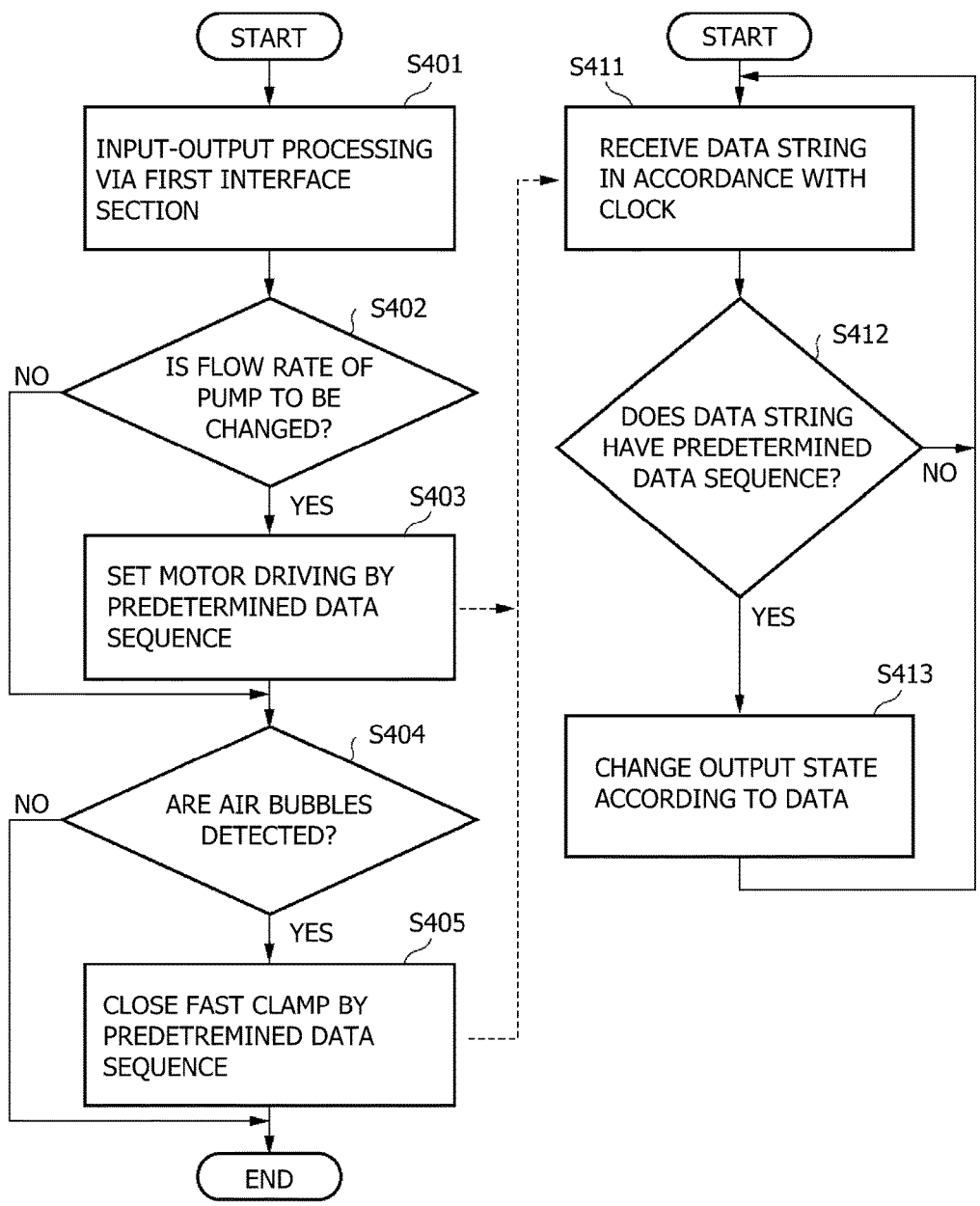
FIG. 4 is a flowchart of assistance in explaining an example of operation of an MPU section 21 using a second interface section.

FIG. 4 is a flowchart of assistance in explaining operation when the MPU section 21 according to the embodiment controls the motor 101 and the fast clamp 110 connected to the MPU section 21 via the I/O expander 26 as the second interface section.

Description will first be made of an outline of operation of the I/O expander 26. The I/O expander 26 receives a data string that is in accordance with a clock signal from the MPU section 21 (for example a data string conforming to I2C communication) via the interface section 25 (step S411). When the received data string has a predetermined data sequence which is recognized as valid, the I/O expander 26 changes an output state according to the data sequence (step S412 and S413). On the other hand, the I/O expander 26 does not change the output state unless the received data string has the predetermined data sequence (NO in step S412). Thus, the output state of I/O expander 26 always corresponds to the last valid command received from MPU section 21. In the event of a failure of MPU section 21, the operation of the mechanism being driven via I/O expander 26 continues indefinitely according to the last valid command. It is to be noted that while the I/O expander 26 is used as the second interface section in the present embodiment, the second interface section is not limited to this. Any constitution may be used as long as the constitution sets the output state according to the predetermined data sequence, as shown in steps S411 to S413, and as long as the second interface section is not affected by the operation of microcomputer monitoring section 22 or by the resetting of MPU section 21 and first interface section 25.

Description will next be made of a part related to the control of the motor 101 and the fast clamp 110 by the MPU section 21. First, the MPU section 21 performs input and output via the first interface section (the interface section 25) (step S401). This processing performs various kinds of display outputs to the display section 204 and captures various kinds of signals such as an air bubble detection signal from the air bubble sensor 107, an operating signal from the operating section 205, and the like into the MPU section 21.

The MPU section 21 determines from the input signals obtained in step S401 whether or not the flow rate provided by the centrifugal pump 102 needs to be changed. When the MPU section 21 determines that the flow rate provided by the centrifugal pump 102 needs to be changed, the MPU section 21 outputs a driving setting value (for example a rotational speed) for the motor 101 in a predetermined data sequence for changing the output state of the I/O expander 26 (steps S402 and S403). It is determined in step S412 that this data has the predetermined data sequence. Thus, the driving setting value set by the MPU section 21 in step S403 is set in the motor driving circuit 203, whereby the driving control of the motor 101 is performed.

The MPU section 21 next determines whether or not an air bubble detection signal is output from the air bubble sensor 107 (step S404). When an air bubble detection signal is output from the air bubble sensor 107 where the fast clamp 110 is in an opened state, then the fast clamp 110 is set in a closed state. For this purpose, the MPU section 21 outputs a data string having a predetermined data sequence for closing the fast clamp 110 to the I/O expander 26 (steps S404 and S405). It is determined in step S412 that this data has the predetermined data sequence. An output for closing the fast clamp 110 is therefore output from the I/O expander 26. When the fast clamp 110 is closed, the blood flow provided by the extracorporeal circulation device is stopped. The closed state of the fast clamp 110 is maintained until the user performs a predetermined restoration procedure.

As described above, in the case where the extracorporeal circulation device 100 is applied as the life support device 10, the output of the second interface section is used to drive the motor for the pump for circulating the blood. Therefore the driving of the pump can be maintained even when the MPU section 21 is in a runaway state or the like. Specifically, while the output of the I/O expander 26 can be updated when the motor or the fast clamp is driven in step S403 or step S405, the output of the I/O expander 26 is seldom updated when the MPU section 21 runs away, for example. The driving of at least the pump necessary for life support is therefore maintained. In addition, in the foregoing embodiment, the fast clamp 110 as clamp means for stopping the circulation of the blood in response to the detection of air bubbles in the extracorporeal circulation path is driven via the second interface section. Such a constitution makes it possible to prevent the fast clamp 110 from being set in a closed state by erroneous operation at a time of runaway of the MPU section 21, and thus maintain the flow of the blood more surely.

It is to be noted that while the extracorporeal circulation device 100 is illustrated as an example of the life support device 10 in the foregoing embodiment, the life support device 10 is not limited to this. For example, an artificial respirator can be applied as the life support device 10. In that case, it suffices to drive various actuators such as a pump, an oxygen blender, and an exhalation valve in a mechanism section of the artificial respirator via the second interface section.

It is to be noted that the communication between the MPU section 21 and the second interface section (the I/O expander 26) has been explained as a serial communication (I2C communication), but is not limited to this. The output state may be set by a parallel communication including a predetermined command.

In addition, a digital signal is used between the second interface section (the I/O expander 26) and the motor driving circuit 203. However, an analog signal or a three-phase driving pulse signal may of course be used between the motor driving circuit 203 and the motor 101.

The present invention is not limited to the foregoing embodiment, but is susceptible of various changes and modifications without departing from the spirit and scope of the present invention. Therefore, in order to make the scope of the present invention public, the following claims are appended.

The invention claimed is:

1. A controller for a life support device for a patient, comprising:
    an actuator for life support operation;
    a sensor for providing a sensor signal in response to life support operation;
    a control section providing sequence control of the life support device, including generating a control state for the actuator in response to the sensor signal;
    a first interface directly connected to the control section and the sensor providing the sensor signal to the control section for generating the control state, wherein a failure of the control section results in failure of the first interface; and
    a second interface connected to the first interface and to the actuator, wherein an output state of the second interface is set in response to a predetermined valid data sequence corresponding to the control state output from the control section to the second interface via the first interface, and wherein the set output state is maintained until the second interface means receives another predetermined valid data sequence for another control state generated by the control section so that the set output state is unaffected by the failure of the control section.

2. The controller for the life support device according to claim 1,
    wherein the life support device is an extracorporeal circulation device, and
    wherein the actuator is a motor for circulating blood.

3. The controller for the life support device according to claim 2, further comprising a clamp for stopping circulation of the blood in response to detection of air bubbles in an extracorporeal circulation path,
    wherein the clamp is connected to the second interface for being controlled by the control section by corresponding predetermined data sequences output from the control section to the second interface via the first interface.

4. The controller for the life support device according to claim 1, further comprising:
    a detector detecting a stop or runaway of the control section; and
    an indicator providing a notification when the detector detects a stop or runaway of the control section;
    wherein the control section and first interface are reset in response to the notification, and wherein the second interface is unaffected by the notification.

5. A method for controlling a life support device having an actuator, a sensor, a control section generating a control state for the actuator in response to the sensor, and a first interface directly connected to the control section and the sensor, wherein a failure of the control section results in failure of the first interface, the method comprising the steps of:
    connecting a second interface comprised of an input/output expander between the first interface and the actuator, wherein the second interface is unaffected by the failure of the control section;
    the control section determining a control state for the actuator;
    the control section sending a predetermined data sequence corresponding to the control state from the first interface to the second interface;
    the second interface checking a validity of a received predetermined data sequence and modifying an output state of the second interface if the received predetermined data sequence is valid, otherwise leaving the output state unmodified, so that a last valid output state is maintained in the event of a failure of the control section.

* * * * *